United States Patent
Akula et al.

(10) Patent No.: US 9,046,524 B1
(45) Date of Patent: Jun. 2, 2015

(54) METHOD TO QUANTIFY AND MEASURE EXCESS COLIPASE IN A PANCREATIN ACTIVE PHARMACEUTICAL INGREDIENT

(71) Applicant: Scientific Protein Laboratories, LLC, Waunakee, WI (US)

(72) Inventors: Anisha Akula, Madison, WI (US); Yan Wang, Middleton, WI (US)

(73) Assignee: Scientific Protein Laboratories, LLC, Waunakee, WI (US)

( * ) Notice: Subject to any disclaimer, the term of this patent is extended or adjusted under 35 U.S.C. 154(b) by 0 days.

(21) Appl. No.: 13/779,523

(22) Filed: Feb. 27, 2013

Related U.S. Application Data (60) Provisional application No. 61/604,800, filed on Feb. 29, 2012.

(51) Int. Cl.
*C12N 9/94* (2006.01)
*G01N 33/68* (2006.01)

(52) U.S. Cl.
CPC . *G01N 33/68* (2013.01); *C12N 9/94* (2013.01)

(58) Field of Classification Search
CPC .............. A61K 49/00; A61K 2121/00; A61K 2123/00; C12N 9/94; G01N 33/573; C12Y 301/01003
See application file for complete search history.

(56) References Cited

PUBLICATIONS

Kelly, D.G. et al. 1991. How to Protect Human Pancreatic Enzyme Activities in Frozen Duodenal Juice. Gastroenterology 100:189-195. specif. 191.*

Gaskin, K.J. et al. 1982. Colipase and Maximally Activated Pancreatic Lipase in Normal Subjects and Patients with Steatorrhea. Journal of Clinical Investigations 69:427-434. specif. 428, 430, 432-433.*
Merriam-Webster Dictionary.Datasheet [online]. Merriam-Webster online Dictionary. Copyright 2014 Merriam-Webster, Inc. [retrieved on Jan. 29, 2014]. Retrieved from the Internet: <URL: http://www.merriam-webster.com/dictionary/pancreatin>.*
Lowe et al. "Assays for Pancreatic Triglyceride Lipase and Colipase", Methods in Molecular Biology, 1998, 109(1), 57-70.
Erlanson et al. "Tributyrine as a Substrate for Determination of Lipase Activity of Pancreatic Juice and Small Intestinal Content", Scand. J. Gastroent., 1970, 5, 293-295.
Brockerhoff, H. "Substrate Specificity of Pancreatic Lipase Influence of the Structure of Fatty Acids on the Reactivity of Esters", Biochim. Biophys. Acta, 1970, 212, 92-101.
Sternby et al. "Degree of in vivo Inhibition of Human Gastric and Pancreatic Lipases by Orlistat (Tetrahydrolipstatin, THL) in the Stomach and Small Intestine", Clinical Nutrition, 2002, 21(5), 395-402.
Hermoso et al. "Neutron Crystallographic Evidence of Lipase-Colipase Complex Activation by a Micelle", The EMBO Journal, 1997, 16(18), 5531-5536.
Gaskin et al. "Colipase and Maximally Activated Pancreatic Lipase in Normal Subjects and Patients with Steatorrhea", J. Clin. Invest., 1982, 69, 427-434.
Hermoso et al. "The Crystal Structure of the Porcine Lipase-Colipase-Tetraethylene Glycol Monooctyl Ether Complex", J. Biol. Chem., 1996, 271(30), 18007-18016.
Imamura et al., Clinical Chemistry, 1989, 35, 1126-1130.

* cited by examiner

*Primary Examiner* — John S Brusca
*Assistant Examiner* — Sharon M Papciak
(74) *Attorney, Agent, or Firm* — Reinhart Boerner Van Deuren s.c.

(57) ABSTRACT

A method for determining the amount of colipase in a pancreatin active pharmaceutical ingredient sample is provided, the method being a titrimetric method with a constant pH and temperature.

5 Claims, 10 Drawing Sheets

METHOD TO QUANTIFY AND MEASURE EXCESS COLIPASE IN A PANCREATIN ACTIVE PHARMACEUTICAL INGREDIENT

FIELD OF THE INVENTION

The present invention relates generally to a method for determining the amount of colipase in a pancreatin active pharmaceutical ingredient sample.

BACKGROUND OF THE INVENTION

Pancreatin is a mixture of several digestive enzymes produced by the exocrine cells of the pancreas. It is composed of amylase, lipase and protease. The pancreas gland produces both endocrine secretions that enter the blood stream and exocrine secretions that enter the duodenum. Whereas the endocrine secretions comprise hormones such as insulin and glucagon, the exocrine secretions to a large part are made up of enzymes necessary for digestion of food in the duodenum.

In particular, pancreatic lipase contains a polypeptide cofactor named colipase. Pancreatic lipase is inactivated by bile salts in the concentrations they occur in the small intestine. The function of colipase is to reactivate bile salt-inhibited lipase. The function of lipase in the intestine depends on the presence of an adequate concentration of colipase. A colipase deficiency could lead to poor digestion and mal-absorption of fat. Colipase has two important surfaces, a hydrophilic surface that interacts with lipase and a hydrophobic surface that presumably interacts with substrate (fat). Hermoso (1996) reported the X-ray structure of the porcine pancreatic lipase (PL)-colipase (CL) complex obtained in the presence of the C8E4 non-ionic detergent (Hermoso, J. et al., *The Journal of Biological Chemistry*, 271, 18007-18016 (1996)).

Colipase has no lipolytic activity of its own, but the lipase activity is proportional to the amount of colipase present ("colipase activity") under physiological conditions, i.e. colipase binds to lipase in a 1:1 molar ratio. Therefore, colipase activity can be defined in operational terms as the capacity to reactivate pure pancreatin lipase in the presence of supramicellar concentrations of bile salt (Gaskin, K. J. et. al., *The Journal of Clinical Investigation*, 69(2): 427-434 (1982)).

The current USP monograph is silent as to colipase and how to test its level in, for example, a pancreatin active pharmaceutical ingredient (API). It is therefore desirable to develop an assay method to measure the amount of colipase present in a pancreatin sample and to verify saturation levels that are present in pancreatin API.

SUMMARY OF THE INVENTION

In light of the foregoing, it is an object of the present invention to provide a method for the detection of colipase in a sample of pancreatin active pharmaceutical ingredient ("API"), the method comprising using a glyceryl tributyrate (GTB) substrate in a titrimetric method with a constant pH and temperature. This method is employed to measure the amount of colipase in a sample of pancreatin API.

It is yet another object of the invention to provide a method to determine the amount of excess colipase in a sample of pancreatin API, the method comprising using an olive oil substrate in a titrimetric method with a constant pH and temperature.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom.

BRIEF DESCRIPTION OF THE FIGURES

FIG. 9 is a graph showing the linear curve of colipase, wherein FIG. 9a is a colipase to lipase molar ratio curve and FIG. 9b is derived from FIG. 9a.

DETAILED DESCRIPTION OF THE INVENTION

Assay Method to Measure the Amount of Colipase in Pancreatin API

Accordingly, the present invention includes a titrimetric method to determine an amount of colipase in a pancreatin API sample. An automatic titrator unit is employed as an instrument both to measure the pH change as a result of the enzyme acting on the substrate and to titrate sodium hydroxide into the reaction mixture to keep a constant pH. A recirculating water bath was used to provide constant temperature (37° C.)

As described herein, three different conditions of lipase activity are optimized: (a) lipase activity is determined as described by Erlanson et al., *Scandinavian J. Gastroenterology*, 5, 293-295 (1970), incorporated herein by reference, using glycerol tributyrin (GTB) as substrate with bile salt (sodium taurodeoxycholate hydrate, TDC) below its critical micellar concentration (CMC); (b) lipase activity against tributyrin is titrated with different concentrations of TDC to determine the CMC for inhibition; and (c) lipase activity is determined in a system in which it is inhibited by TDC bile salt and reactivated by an excess of added colipase.

The optimum concentration of bile salt (below CMC) to measure total lipase activity is 1 mM Na-TDC. The working concentration of bile salt to inhibit the lipase activity is 4 mM Na-TDC (above CMC). The optimum concentration of colipase to restore the inhibited lipase activity is 2.5 µg (0.083 µg/mL) per reaction.

Colipase has previously been reported to affect the activity of lipase in the absence of bile salts. With tributyrin as substrate, a small and varying increase in lipase activity (1.2 to 2.0 fold) is reported for the addition of colipase (Borgstrom, B. "Lipases" edited by B. Borgstrom and H. Brockman, Elsevier Science Publishers B. V., The Netherlands, pp. 152-183 (1984); incorporated herein by reference). In the absence of bile salt, colipase also helps to stabilize lipase and decrease its rate of inactivation in the presence of substrate. Colipase binds to lipase in a 1:1 molar ratio and also binds to the bile salt-covered triacylglycerol interface, in this way anchoring lipase to its substrate by fixing it to the lipid-water interface. Colipase at higher concentration inhibits lipolysis, an effect that may be due to competition for the interface or to a binding of lipase to colipase in the aqueous phase. The colipase content of the sample is determined as a difference between two titration values, the blank with lipase and the test with lipase plus added known colipase or sample with unknown amount of colipase.

Figure 1:
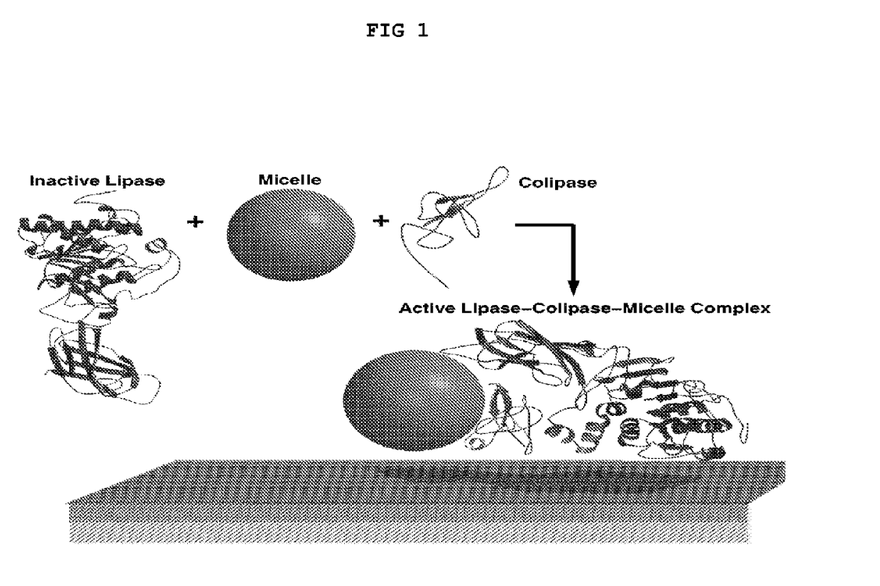
FIG. 1 is a schematic depiction of lipase activation in solution by colipase and a micelle (bile salt).

The main function of colipase is to restore the activity of lipase in the presence of bile salt above the CMC. The effect of conjugated bile salts on activity of pancreatin lipase depends on their concentration relative to their CMC. At low concentration (below CMC), conjugated bile salts protect lipase from temperature inactivation and also stimulate the initial rate of hydrolysis of tributyrin. Above the CMC, conjugated bile salts inhibit lipase activity. Bile salt inhibition of lipase is related both to the concentration of bile salt and to the substrate concentration or rather to substrate surface area. The presence of bile salts protects the enzyme from being irreversibly inactivated and may stabilize the lipase structure. FIG. 1 represents the lipase activation and process of lypolysis (see also Hermosa, J. et al., *EMBO J.* 16, 5531-5536 (1997), incorporated herein by reference).

Accordingly, the invention utilizes a continuous titration with pH-Stat coupled to an automatic burette, as described by Junge, W., "Lipases. Pancreatic lipase. Titrimetric method, in Enzymes 2: Esterases, Glycosidases, Lyases, Ligases, Vol. 4," *Methods of Enzymatic Analysis* edited by Moss, D. W., Verlag Chemie, Basel, pp. 15-25, all of which are incorporated herein by reference. Preferably, either diglyceride (Imamura, S. et al., *Clinical Chemistry*, 35, 1126-1130 (1989), incorporated herein by reference) or triglyceride is employed, and more preferably a triglyceride. Suitable triglycerides for use in the titrimetric method disclosed herein include, but are not limited to, triolein, trioctanoin, tributyrin, and the like. Such tryglicerides are hydrolyzed by lipase (Brockerhoff, H. et al., *Biochem. Biophys. Acta* 212, 92-101 (1970), incorporated herein by reference). More preferably, tributyrin (GTB) is used as the substrate.

Figure 2:
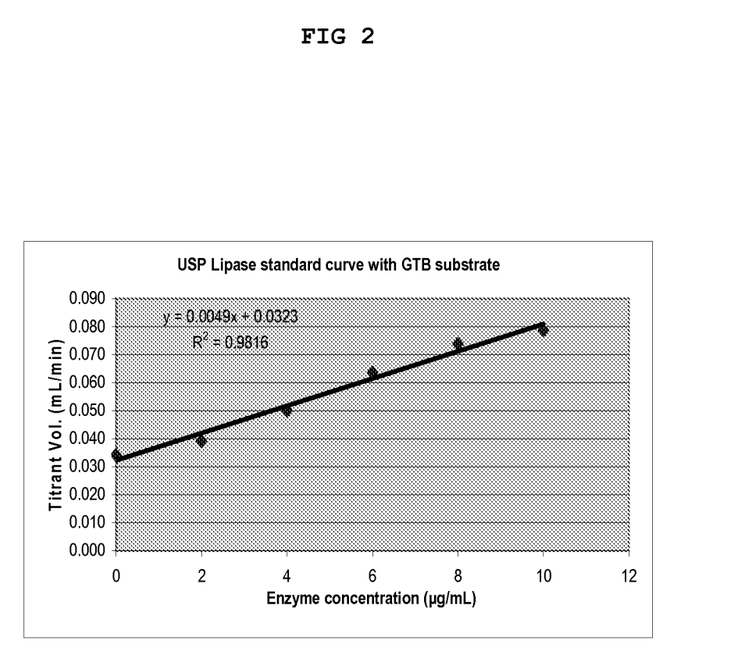
FIG. 2 is a graph depicting the linear range of lipase between 2-10 µg/mL.

In a specific aspect of the invention, the assays are performed using a DL 53 Titrator for five minutes at 37° C. in a glass mixing chamber with 30 mL of substrate mix containing 1 mM Na-TDC at pH 7.5. A range from 2.0-500 μg/mL USP lipase with GTB substrate is tested. As illustrated in FIG. 2, the linear range at the lowest end is found to be 2.0-10.0 μg/mL with linearity ($R^2$) of 0.9816.

Figure 3:
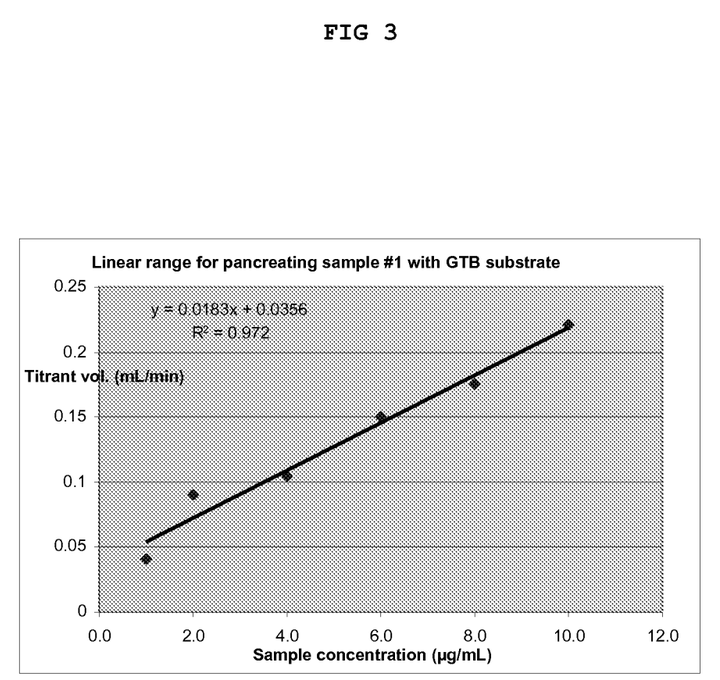
FIG. 3 is a graph depicting the linear range of pancreatin sample #1 between 1.0-10 µg/mL.

Similarly, the linear range of pancreatin API sample can also be determined. Specifically, the assays are performed for kinetic reaction for five minutes at 37° C. in a glass mixing chamber with 30 mL of substrate mix containing 1 mM Na-TDC at pH 7.5. The lowest concentration for the working range of Pancreatin API sample is determined; a concentration range from 1.0 to 10 μg/mL for pancreatin sample #1 is tested using GTB substrate. Data is calculated for rate against enzyme concentration and as illustrated in FIG. 3, the linear range for Pancreatin API is 1.0 to 10 μg/mL ($R^2$=0.97).

Figure 4:
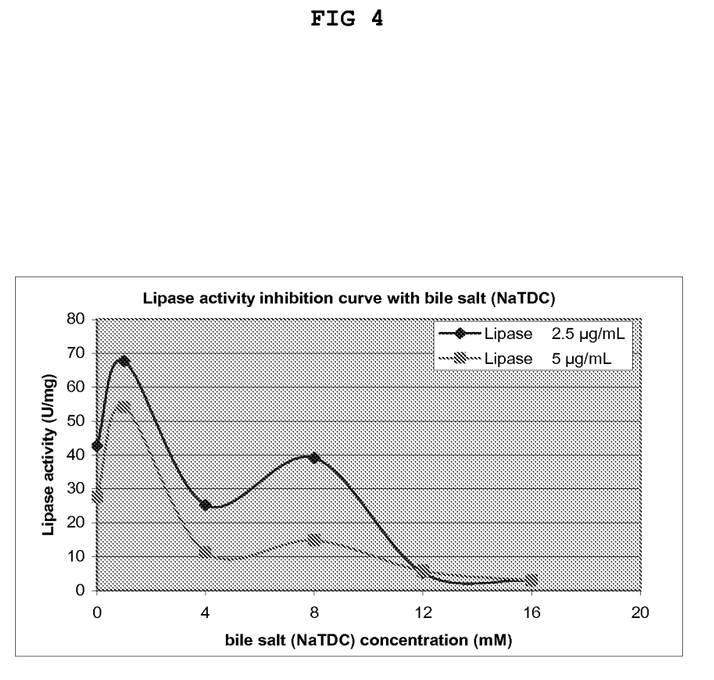
FIG. 4 shows the bile salt inhibition of lipase activity from 4 mM Na-TDC.

Lipase activity against tributyrin is assayed with different concentration of TDC to determine the CMC for inhibition. The minimum TDC concentration to achieve sufficient inhibition of lipase activity is determined. Five different concentrations (1, 4, 8, 12 and 16 mM) of sodium taurodeoxycholate (Na-TDC) are used to determine the CMC of bile salt on two concentrations of lipase (2.5 and 5.0 μg/mL). FIG. 4 shows that below the CMC (1 mM Na-TDC), the conjugated bile salts slightly stimulate the initial rate of hydrolysis. As shown also in FIG. 4, increasing the concentration of bile salt above the CMC results in a progressive inhibition of lipase activity (4-16 mM Na-TDC). An enhancement in lipase activity is observed when the bile salt is used below CMC (1 mM Na-TDC) compared to the activity produced without the bile salt (0 mM Na-TDC). In contrast, when the bile salt is used above the CMC (4, 8, 12 & 16 mM Na-TDC), almost complete inhibition of lipase activity is observed. The lipase inhibition with higher concentration of bile salt (above CMC) is more consistent with the lipase at 5.0 μg/mL when compared to 2.5 μg/mL lipase (FIG. 4).

In yet another embodiment, the effect of colipase on lipase activity and determination of the optimum concentration of colipase to measure the restored lipase activity is studied. The method for colipase determination is based on the principle that lipase inactivated by bile salt is reactivated by colipase (FIG. 1). FIG. 4 supports the theory of reactivation of lipase with the addition of exogenous colipase. As such, different concentrations of bile salt (0, 4, 8, 12 and 16 mM) are tested in the presence of 5.0 μg of lipase per reaction to measure the lipase activity. To each reaction beaker, a different amount of colipase (2.5, 5.0 and 10 μg) is added to the assay mixture prior to the lipase.

Figure 5:
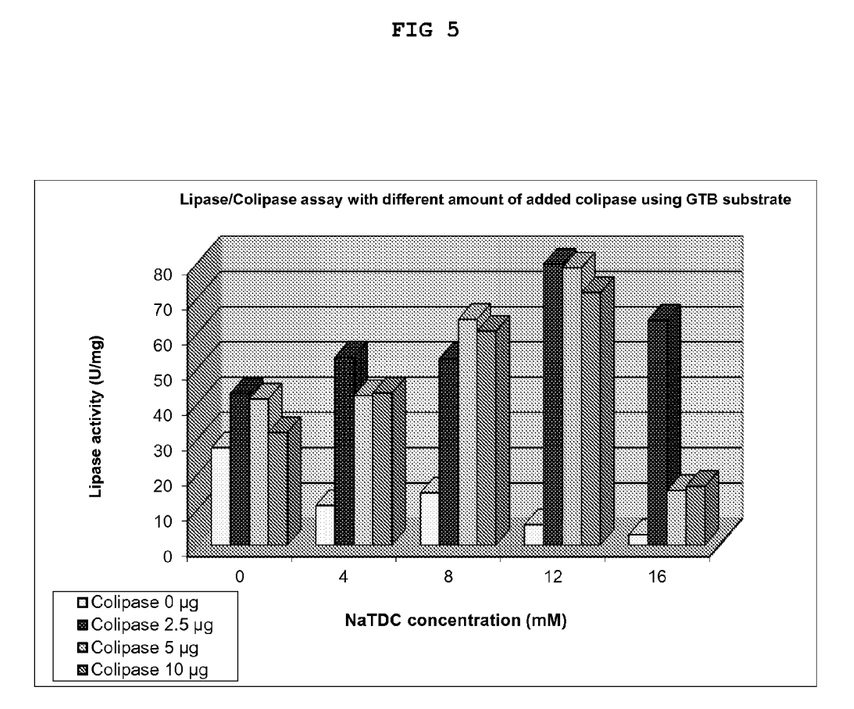
FIG. 5 shows the restored lipase activity measured with added colipase.

As shown in FIG. 5, increasing concentration of Na-TDC (0, 4, 8, 12, and 16 mM) results in a progressive inhibition of lipase. However, by adding different concentration of exogenous colipase (Sigma Cat #C3028), lipase activity is restored. In FIG. 5, 2.5 μg colipase, 5.0 μg colipase, and 10.0 μg colipase bars with 4, 8, 12 and 16 mM Na-TDC represent the lipase activity due to reactivation of lipase from addition of exogenous colipase. The presence of colipase at higher concentration will inhibit lypolysis. The 10 μg colipase in FIG. 5 shows lower activity when compared to 2.5 and 5.0 μg colipase, supporting the theory. FIG. 5 reveals that the restored lipase activity in the presence of 16 mM TDC with 5 and 10 μg colipase is 4-fold lower than the lipase activity obtained with 2.5 μg colipase. Although the main function of colipase is to restore the activity of the bile salt-inhibited lipase, colipase also has been reported to affect the activity of lipase in absence of bile salts by stabilizing lipase and decreasing its rate of inactivation in the presence of substrate (see Borgstrom and Brockman, 1984). The results show that without bile salt there is about 1.5-fold increase in the lipase activity by addition of 2.5 μg colipase (FIG. 5, Point 0). Results reveal the most favorable amount of colipase to recover the inhibited lipase is 2.5 μg per assay with 4 mM Na-TDC.

In still another embodiment, a separate study is performed with differing amounts of lipase (2.5, 5.0 and 10 μg per reaction) to determine the maximum recovery of lipase activity in the presence of 4 mM Na-TDC and 2.5 μg added colipase. The colipase content of the sample is determined as a difference between two titration values, the blank with lipase and the test with lipase plus added colipase (test values–blank values). The accuracy of the determination is dependent on the relative proportion between lipase and colipase.

Figure 6:
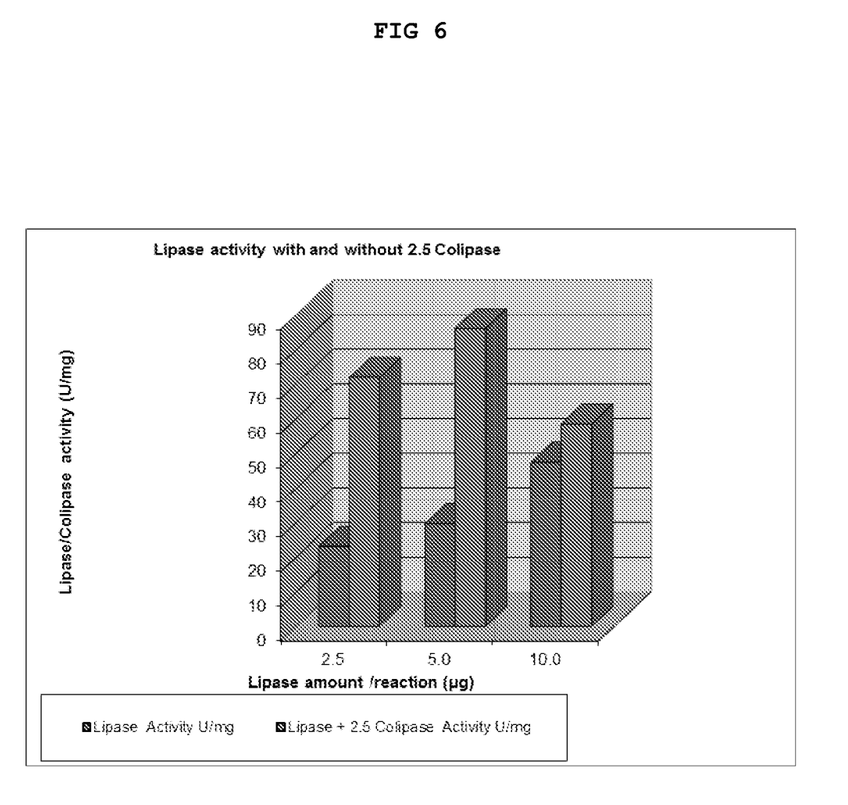
FIG. 6 depicts the lipase activity with and without 2.5 µg colipase in the presence of 4 nM Na-TDC.

FIG. 6 shows the activity relationship for colipase (2.5 μg) with three different levels of lipase corresponding to 2.5, 5.0, and 10 μg lipase added per reaction vessel. The activity in the absence of added colipase increases with increase in lipase amount, due to presence of endogenous colipase. Further, the lipase activity increases by adding exogenous colipase. Results show two-fold increase in restored lipase activity at 2.5 and 5.0 μg of lipase, whereas restored lipase activity at 10.0 μg lipase is only 0.23 fold, which could be due to inhibition from over-saturation of colipase concentration (FIG. 6). The results confirm that the optimum amount of lipase with 2.5 μg colipase at 4 mM Na-TDC is 5 μg per reaction as seen in FIG. 5.

Figure 7:
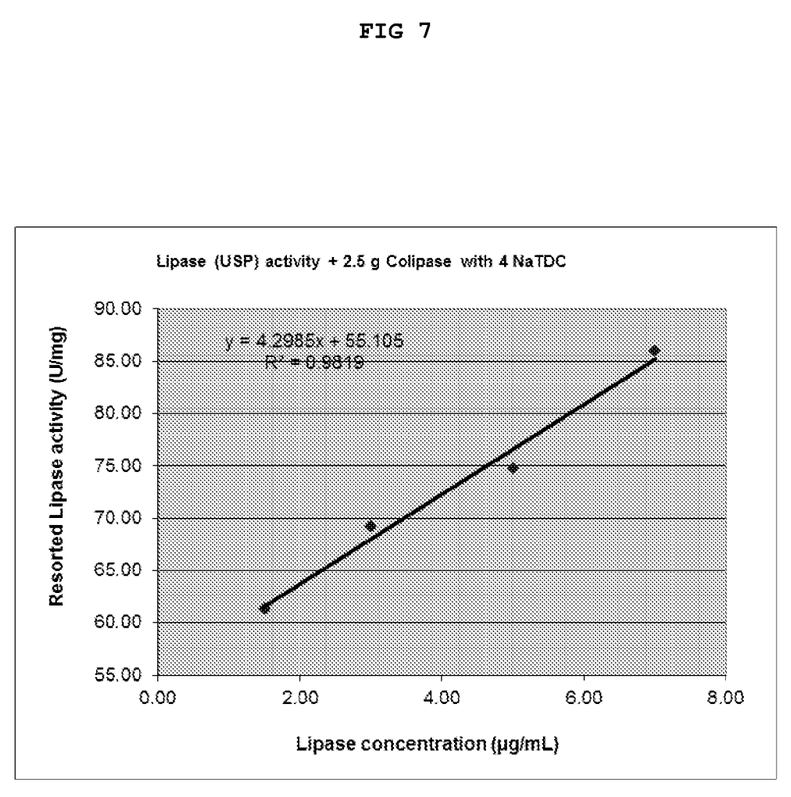
FIG. 7 shows the lipase activity plus 2.5 µg colipase with 4 Na-TDC.

As discussed above, it is known that colipase binds to lipase in a 1:1 molar ratio. Additionally, the amount of colipase must be added in a two to five-fold molar excess to lipase to restore the lipase activity (Lowe et al., *Methods in Molecular Biology*, 109(I): 57-70 (1998), incorporated herein by reference). If the amount of colipase is in excess, activity is expected to be linear with increasing amounts of the lipase added to the assay. Based on the above results, the working amount of colipase for the chosen conditions is determined as 2.5 µg. Another study is performed with different amounts of lipase (1.5, 3.0, 5.0 and 7.0 µg/mL) to measure the lipase activity in the presence of 4 mM bile salt (Na-TDC) and 2.5 µg added colipase. FIG. 7 reveals a linear increase in lipase activity with increase of lipase concentration in the presence of 2.5 µg colipase, indicating the amount of colipase chosen is in excess. As the linear range for lipase with 2.5 µg of added colipase is very narrow (1.5-7.0 µg), only four concentrations of lipase are tested. To this end, FIG. 6 shows that 10 µg lipase is out of linear range.

Assay Method to Measure Excess Amount of Colipase

In yet another embodiment of the invention, an analytical method is provided to determine the excess amount of colipase present in pancreatin API sample using olive oil as substrate. This method is used to quantify excess amount of colipase present in a pancreatin API sample.

In order to quantify the excess amount of colipase present in a pancreatin API sample, two different conditions of lipase activity are optimized: 1) standard curve for colipase using Sigma porcine colipase as an external standard spiked with fixed amount of pure porcine lipase (PPL); and 2) the lipase activity with olive oil is titrated with different amount of PPL spiked with fixed amount of pancreatin API sample.

Figure 9:
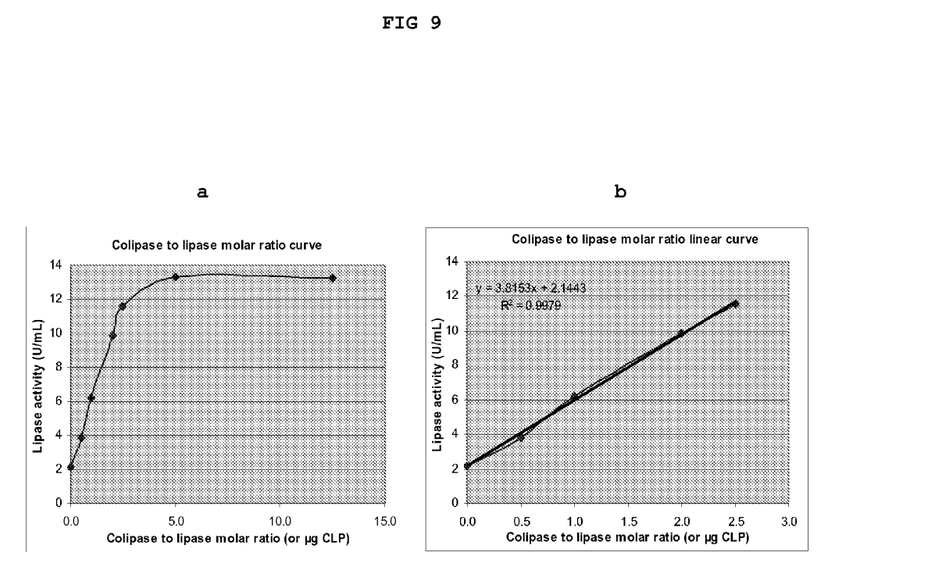

A range between 0.0 and 12.5 µg/mL Sigma colipase spiked with 5.0 µg/mL PPL using olive oil as a substrate is tested (FIG. 9a). Data is calculated for linearity ($R^2$) for rate against enzyme concentration. As illustrated in FIG. 9b (derived from FIG. 9a), the linear range is found between 0.0 and 0.0025 mg/mL with linearity ($R^2$) of 0.9979.

As mentioned above, pancreatin colipase binds to lipase in a 1:1 ratio and is adequate for maximum lipase activity. The molecular size of colipase is about 20% of pancreatin lipase. Thus, if 5.0 µg of pure pancreatin lipase is assayed, 2.5 µg of colipase provides a 2.5-molar excess of colipase.

Figure 10:
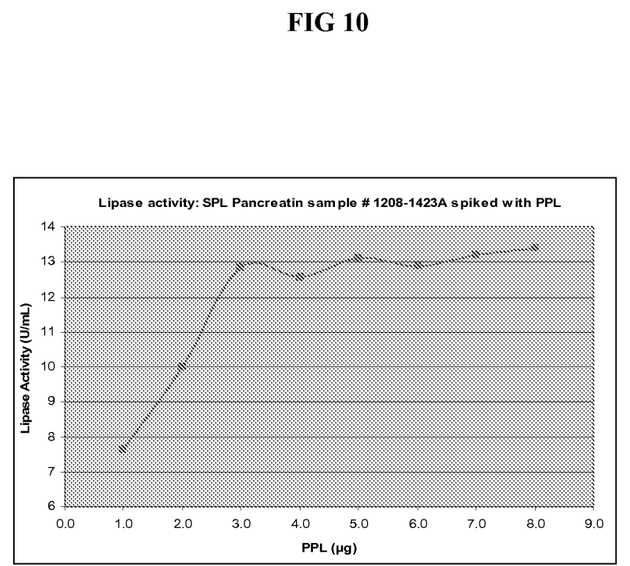
FIG. 10 shows the lipase activity in pancreatin sample #1 spiked with different amounts of pure porcine lipase.

Thus, in an embodiment of the invention, an analytical method demonstrates the increase in lipase activity due to an excess of colipase present in a pancreatin API sample when a sample is spiked with a different amount of PPL. After the point where 100% of the colipase present in a pancreatin API sample is consumed for lipase activity, no further increase in lipase activity is measured, in spite of the sample spiked with higher amount of PPL. The lipase activity is measured with a fixed amount of pancreatin sample spiked with different amounts of PPL (0.0 to 0.0059 mg per reaction). As shown in FIG. 10, there is an initial increase in lipase activity with increasing amount of PPL (first three points). However thereafter, no significant increase in lipase activity is observed. Thus, as long as colipase is available to the pancreatin sample spiked with PPL for lipase activity, an increase in lipase activity is observed. Once 100% of the colipase is utilized, no further increase in lipase activity is observed.

EXAMPLES

Example 1

Method of Measuring Amount of Colipase in a Pancreatin Sample

1) Reference Standard: USP Lipase Cat #1494079 Lot I1E327 purchased from USP Rockville, Md. Labeled lipase activity is 21.2 U/mg using USP method (olive oil as a substrate); 2) Colipase Standard: Sigma Colipase from porcine pancreas Cat #C3028 (Sigma CF 100% pure); 3) Instrumentation: A Mettler Toledo DL 53 Titrator connected with pH meter, automatic 5 mL burette, temperature sensor, and a stirrer is used to study the lipase/colipase enzyme system that hydrolyzes tributyrin (GTB) substrate.

Pancreatin samples #1, #2 and #3 are prepared free of lipase activity by incubating each sample at 75° C. for 0, 15 and 30 minutes. The optimum time required to inactivate lipase in pancreatin sample is 30 minutes and the amount of sample (with unknown colipase) required to measure colipase is between 0.05 to 0.15 mg per reaction. The lipase activity is measured in lipase units with and without spiking a known amount of colipase (2.5 µg) and unknown amount of colipase (50 to 150 µg) per reaction. The assays are performed for five minutes at 37° C. in a glass mixing chamber with 30 mL of substrate mix containing 4 mM Na-TDC at pH 7.5. Since colipase has no lipolytic activity of its own, the lipase activity is proportional to the amount of colipase present ("colipase activity") under physiological conditions. The ratio of lipase activity obtained from lipase spiked with unknown and lipase spiked with known amount of colipase provides amount of colipase present in pancreatin sample. Table 1 shows the measured value of colipase in pancreatin sample.

TABLE 1

| Run | #1 mg Colipase/ g panc DW | #2 mg Colipase/ g panc DW | #3 mg Colipase/ g panc DW |
| --- | --- | --- | --- |
| Day 1 | 12.47 | 9.82 | 8.89 |
|  | 13.34 | 9.71 | 8.66 |
| Day 2 | 11.28 | 8.18 | 8.82 |
|  | 11.46 | 8.70 | 8.04 |
| Average | 12.14 | 9.10 | 8.40 |
| Std. Dev. | 0.9576 | 0.7952 | 0.57 |
| % RSD | 7.9 | 8.7 | 6.7 |

To check the precision of the assay method to measure lipase activity, three independent substrate mixtures are prepared by two analysts on the same day. Each substrate mix is used with two independent sample preparations (two weighings) of USP Lipase at a concentration of 5.0 µg/mL, and each is run in triplicate to give six data points per substrate mix and a total of eighteen data points for three independent substrate mixture preparations. The average lipase activity from independent sample preparations run in triplicate is between 48.12 U/mg and 57.97 U/mg with % RSD between 2.2 and 13.7%. In order to check the reliability of the method developed, a statistical analysis (ANOVA) at confidence level 95% is performed. The ANOVA shows that the p value is 0.23. Since the p-value is greater than 0.05, it suggests no statistically significant difference in mean lipase activities measured at three independent times (Table 2) by two analysts.

TABLE 2

| | 1 mM NaTDC | | | | | |
| --- | --- | --- | --- | --- | --- | --- |
| | Substrate mix-1 | | Substrate mix-2 | | Substrate mix-3 | |
| Replicate | USP Lipase Pre-I | USP Lipase Prep-II | USP Lipase Prep-I | USP Lipase Prep-II | USP Lipase Prep-I | USP Lipase Prep-II |
| 1 | 52.31 | 50.87 | 51.17 | 48.71 | 46.81 | 50.78 |
| 2 | 54.88 | 61.77 | 44.95 | NA | 46.79 | 44.78 |
| 3 | 50.84 | 61.26 | 48.24 | 50.27 | 58.84 | 53.73 |
| Average | 52.68 | 57.97 | 48.12 | 49.49 | 50.81 | 49.76 |

TABLE 2-continued

| | 1 mM NaTDC | | | | | |
|---|---|---|---|---|---|---|
| | Substrate mix-1 | | Substrate mix-2 | | Substrate mix-3 | |
| Replicate | USP Lipase Pre-I | USP Lipase Prep-II | USP Lipase Prep-I | USP Lipase Prep-II | USP Lipase Prep-I | USP Lipase Prep-II |
| Std. Dev. | 2.04 | 6.15 | 3.11 | 1.10 | 6.95 | 4.56 |
| % RSD | 3.9 | 10.6 | 6.5 | 2.2 | 13.7 | 9.2 |

To check the precision of the assay method to measure content of colipase in the product, experiments are performed on two different days. For the first day, three independent substrate mixtures and three independent samples (#1) are prepared. On the second day, two independent substrate mixtures and two independent samples (#1) are prepared. Each substrate mix is run in triplicate to give nine data points per day (total of 15 data point for two days). The assay is performed with 5 µg lipase with and without 2.5 µg added colipase, or with 50 to 75 µg of test sample (unknown) in the presence of 4 mM Na-TDC per reaction in all cases. The average amount of colipase measured is between 12.75 and 11.98 mg/g pancreatin dry weight with % RSD of 13.7 and 9.2 (Table 3). In order to check the reliability of the method developed, a statistical analysis (t-test) at confidence level 95% is performed. The t-test shows the p value is 0.3586>0.05, suggesting no statistically-significant difference in mean amount of colipase measured on two different days.

TABLE 3

| | mg Colipase content/g Panc | |
|---|---|---|
| Preparation No. | Day 1 mg/g | Day 2 mg/g |
| Prep 1 | 12.29 | 10.99 |
| | 8.66 | 11.71 |
| | 14.74 | 12.66 |
| Prep 2 | 13.55 | 13.03 |
| | 13.52 | 10.46 |
| | 13.82 | 13.03 |
| Pre 3 | 12.25 | NA |
| | 12.37 | NA |
| | 13.51 | NA |
| Average | 12.75 | 11.98 |
| Std. Dev. | 1.74 | 1.10 |
| % RSD | 13.7 | 9.2 |

For the purpose of accuracy, the amount of colipase present in pancreatin sample #1 is determined. The same sample is then spiked with 0.25 µg of colipase and the total colipase amount (sample+spike) is measured. This recovery study is performed in quadruplicate. Table 4 illustrates the theoretical amount of colipase present in sample #1, the actual measured amount of colipase present in spiked sample (sample #1+0.25 µg colipase) and the % recovery. The data indicates an average 95.5% recovery ranging from 87.10 to 101.37% and a % RSD of 6.5%, showing accuracy for the method.

TABLE 4

| Theoretical amount of colipase µg | Recovered colipase from spiking µg | % Recovery of Colipase |
|---|---|---|
| 0.2502 | 0.2179 | 87.10 |
| 0.2502 | 0.2536 | 101.37 |
| 0.2502 | 0.2373 | 94.88 |
| 0.2502 | 0.2465 | 98.55 |

TABLE 4-continued

| Theoretical amount of colipase µg | Recovered colipase from spiking µg | % Recovery of Colipase |
|---|---|---|
| Average µg | 0.2388 | 95.48 |
| Std. Dev. | 0.0155 | 6.18 |
| % RSD | 6.5 | 6.5 |

To check the specificity of the substrate GTB, an inhibition experiment is conducted with the specific inhibitor Orlistat (Tetrahydrolipstatin, THL, Sigma #04139). The Orlistat inhibits the activities of all gastric/pancreatic lipases except pancreatic phospholipase $A_2$ (Sternby et. al., *Clinical Nutrition*, 21(5), 395-402 (2002), incorporated herein by reference). Reverse phase high-performance liquid chromatography (RP-HPLC) data demonstrated the presence of pancreatin lipase and phospholipase-A2 in pancreatin API samples (#1, #3 and #4) and USP Lipase standard. According to RP-HPLC, cholesterol esterase is not detected in pancreatin API samples. To check the specificity of GTB substrate, bile salt below CMC concentration (1 mM Na-TDC) is chosen to obtain maximum lipase activity.

Figure 8:
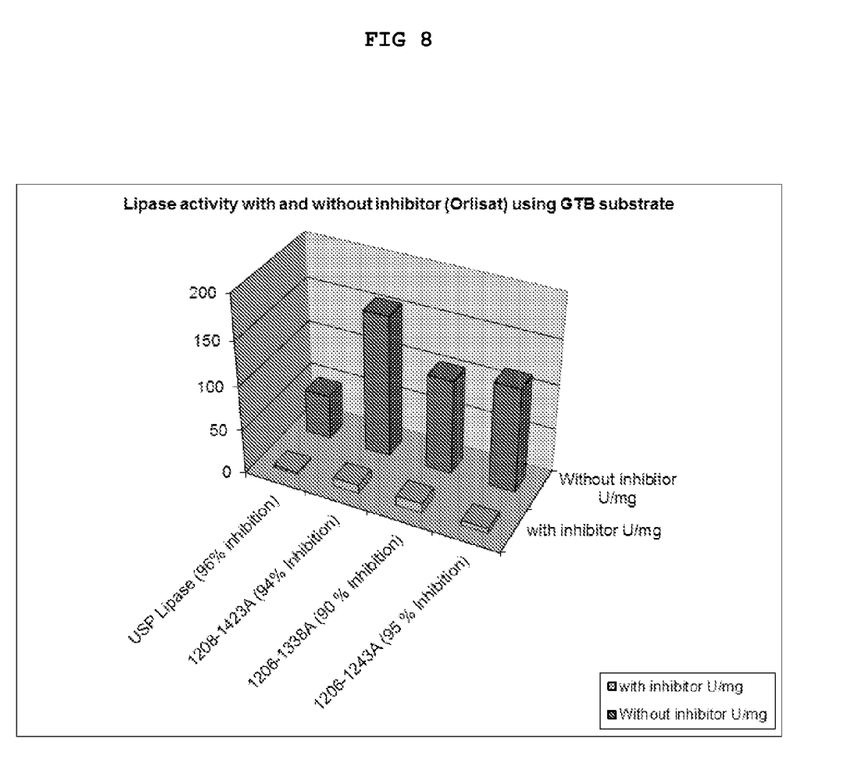
FIG. 8 shows lipase activity measured with and without lipase inhibitor (Orlistat).

The Orlistat is dissolved in dimethyl sulfoxide (DMSO) to obtain 1.0 mg/mL stock solution. Lipase (USP) and pancreatin samples #1, #2 and #3 are mixed with Orlistat at equal molar concentrations (1.0 µM Lipase:Orlistat) and incubated for 5 minutes on ice. The assays are performed on USP Lipase and pancreatin API samples with and without Orlistat. All the samples are titrated with 0.005 M NaOH for 5 minutes in a glass mixing chamber with 30 mL of substrate mix containing 1 mM Na-TDC at 37° C. temperature and pH 7.5. FIG. 8 shows the complete lipase activity and the inhibition 90%) of lipase activity in the presence of Orlistat (lipase inhibitor). This confirms that the pancreatin lipase hydrolyses GTB substrate and substrate GTB is specific for lipase.

Example 2

Method of Measuring Excess Amount of Colipase in a Pancreatin API Sample

1) Reference Standard: USP Lipase Lot #I1E327 and Lot J0G363 purchased from USP Rockville, Md. Labeled lipase activity is 21.2 U/mg for lot #I1E327 and 93.3 U/mg for lot #J0G363 using USP method (olive oil as a substrate); 2) Colipase Standard: Sigma colipase from porcine pancreas Cat #C3028 (Sigma CF 100% pure) is used as an external standard; 3) Pure Porcine Lipase: Pure porcine lipase is obtained from Frèdèric Carrière, UPR 9025 CNRS-Institut de Biologie Structurale et Microbiologie, 13402 Marseille Cedex 20, France. Labeled lipase activity is 2973±96 USP U/mg; and 4) Instrumentation: A Mettler Toledo DL 53 Titrator connected with pH meter, automatic 5 mL burette temperature sensor.

Pancreatin samples #1, #5, #6, #7 and #8 are prepared in duplicates at 8 Units/mL (potency unit). The lipase activity is measured in USP lipase units with and without spiking a known amount of PPL per reaction. The assays are performed for five minutes at 37° C. in a glass mixing chamber with 30 mL of substrate mix pH 9.0 using USP lipase assay method. The average of duplicate results is presented in Table 5. The molar ratio and quantification of excess amount of colipase is calculated using standard curve in FIG. 9*b*. The study results demonstrated that the pancreatin samples are saturated and the average molar ratio of colipase to lipase is 1.4:1.0. The study results also quantified the excess amount of colipase present in pancreatin API samples. Table 5 shows the excess amount of colipase in SPL pancreatin API sample.

TABLE 5

| | Equation obtained from Colipase standard curve: Y = 3.8153x + 2.1443 | | | | | | |
|---|---|---|---|---|---|---|---|
| Pancreatin API Sample # | PPL 0.0 μg (A)* U/mL | Colipase to Lipase molar ratio (C:L) | PPL 2.95 μg (B)** U/mL | Increased Activity (B-A) U/mL | Excess colipase*** μg | Excess amount colipase/mg (dw) Panc sample μg/mg Panc. | % Excess of Colipase |
| #1 | 7.64 | 1.4:1 | 12.59 | 4.95 | 0.7354 | 8.10 | 64.79 |
| #5 | 6.28 | 1.1:1 | 11.62 | 5.34 | 0.8386 | 9.79 | 85.03 |
| #6 | 8.49 | 1.7:1 | 12.62 | 4.13 | 0.5208 | 5.85 | 48.65 |
| #7 | 7.65 | 1.4:1 | 10.38 | 2.73 | 0.1543 | 1.74 | 35.69 |
| #8 | 7.61 | 1.4:1 | 10.58 | 2.97 | 0.2160 | 2.43 | 39.03 |

*Lipase activity measured in pancreatin sample without adding PPL
**Lipase activity measured in pancreatin sample spiked with PPL
***Excess amount of colipase calculated using equation obtained from CLP standard curve e.g Excess colipase μg = [(B-A) − 2.1443]/3.8152

Example 3

Determination of the Amount of Colipase Required for Spiking

To determine the amount of colipase required for spiking, pancreatin API sample #1 is used. Per data, lipase activity for sample #1 is 91 U/mg.

An amount of sample #1 comparable to approximately 1,600 units of lipase activity (based on estimated activity value) is used. The sample has an estimated lipase activity value of 91 U/mg; 1,600 Units=17.58 mg sample required 91 U/mg. 3×17.58 mg, or 53 mg, of sample is actually used by performing a dilution prior to assaying the sample. As such, 53 mg of sample #1 is dissolved in 200 mL of cold, purified water, giving a stock solution of 0.265 mg/mL, or 24.12 U/mL. The stock solution is then diluted to afford 0.09 mg/mL, or 8 U/mL. Similar to that described in Example 1, 1 mL (0.09 mg) of #1 is added to the substrate in a reaction vessel to measure lipase activity.

Theoretically lipase and colipase bind in an equal molar ratio (1:1). The molecular weight of lipase is 50,000 and colipase is 11,000. In other words, 50 mg of lipase should have 11 mg of colipase to provide equal molar amount. For calculation purposes, it is assumed that the sample has lipase equal to 0.09 mg/mL.

If 50 mg lipase contains 11 mg colipase, then 0.09 mg lipase should have 0.02 mg colipase (11×0.09/50). Therefore, 10-25% of assumed amount of colipase (0.002-0.005 mg colipase) is adequate to perform the study. A preliminary study is performed with 0.002 mg and 0.005 mg colipase spiked to 0.09 mg pancreatin sample per reaction. Study results demonstrate statistically no significant difference between lipase activity obtained by spiking 0.002 and 0.005 mg colipase.

The lipase activity in twelve batches of pancreatin API samples is measured with and without planned deviation of spiking sample either with PW or colipase. Lipase activity is performed as per Table 6.

TABLE 6

| Assay | Substrate mL | Sample (8 U/mg) mL | Colipase (0.025 mg/mL) mL | PW mL |
|---|---|---|---|---|
| Control | 29 | 1 | 0.0 | 0.08 |
| Test | 29 | 1 | 0.08 | 0 |

In order to check if a statistically-significant difference existed between lipase activities obtained with and without colipase, a statistical analysis (t-test) at confidence level 95% is performed. The t-test result for ten out of twelve samples shows the p-value is more than 0.05, suggesting no statistically significant difference in mean activity of lipase measured with and without colipase. The p-value for pancreatin sample #9 (p=0.019) and sample ID #10 (p=0.0493) is less than 0.05, suggesting statistically-significant difference in mean of lipase activity. This statistical difference could be due to the small number of replicates (2 replicates). Results are given in Table 7.

TABLE 7

| Sample | Replicate | Lipase Value (U/mg) | Lipase + Colipase Value (U/mg) | Lot Average Lipase (U/mg) | Lot Average Lipase + Colipase (U/mg) | Difference (U/mg) | % Difference |
|---|---|---|---|---|---|---|---|
| #11 | 1 | 41 | 42 | 41 | 41 | 0 | 0% |
| #11 | 2 | 41 | 40 | | | | |
| #2 | 1 | 69 | 69 | 69 | 68.5 | −0.5 | −1% |
| #2 | 2 | 69 | 68 | | | | |
| #12 | 1 | 83 | 86 | 85.5 | 84.5 | −1 | −1% |
| #12 | 2 | 88 | 83 | | | | |
| #13 | 1 | 89 | 94 | 88.5 | 90.5 | 2 | 2% |
| #13 | 2 | 88 | 87 | | | | |
| #14 | 1 | 64 | 63 | 64.5 | 63.5 | −1 | −2% |
| #14 | 2 | 65 | 64 | | | | |
| #15 | 1 | 102 | 101 | 103 | 101.5 | −1.5 | −1% |
| #15 | 2 | 104 | 102 | | | | |
| #16 | 1 | 74 | 75 | 73.5 | 74 | 0.5 | 1% |
| #16 | 2 | 73 | 73 | | | | |

TABLE 7-continued

| Sample | Replicate | Lipase Value (U/mg) | Lipase + Colipase Value (U/mg) | Lot Average Lipase (U/mg) | Lot Average Lipase + Colipase (U/mg) | Difference (U/mg) | % Difference |
|---|---|---|---|---|---|---|---|
| #17 | 1 | 67 | 64 | 67 | 63.5 | −3.5 | −5% |
| #17 | 2 | 67 | 63 | | | | |
| #5 | 1 | 59 | 59 | 59.5 | 58.5 | −1 | −2% |
| #5 | 2 | 60 | 58 | | | | |
| #18 | 1 | 72 | 66 | 70.5 | 67 | −3.5 | −5% |
| #18 | 2 | 69 | 68 | | | | |
| #19 | 1 | 113 | 108 | 113 | 106.5 | −6.5 | −6% |
| #19 | 2 | 113 | 105 | | | | |
| #20 | 1 | 74 | 69 | 73 | 70 | −3 | −4% |
| #20 | 2 | 72 | 71 | | | | |
| | | | | | Average | −1.6 | −2% |

Since there is no enhancement in lipase activity with added exogenous colipase, it is convincingly demonstrated that the pancreatin API samples tested are saturated with colipase.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A method of measuring an amount of colipase in a pancreatin active pharmaceutical ingredient (API) sample comprising:
   i) incubating a pancreatin API sample for a time sufficient to prepare a sample free of lipase activity and containing an unknown amount of colipase;
   ii) adding the incubated pancreatin API sample to a substrate comprising glycerol tributyrin (GTB) and sodium taurodeoxycholate hydrate (TDC) to afford a sample solution;
   iii) titrating the sample solution with a solution of sodium hydroxide at a constant temperature to maintain a certain pH for a period of time;
   iv) generating a titration value from step iii) in ml/minute;
   v) repeat steps ii)-iii) for a standard lipase sample containing a known amount of lipase;
   vi) generating a titration value from step v) in ml/minute; and
   vii) calculating colipase content of the pancreatin API sample as a difference between the titration value from step vi) and the titration value from step iv).

2. A method according to claim 1 wherein the pancreatin API sample is incubated for 30 minutes.

3. A method according to claim 1 wherein each adding and titrating step, collectively, is performed for five minutes.

4. A method according to claim 3 wherein the temperature is maintained at 37° C.

5. A method according to claim 3 wherein the pH is maintained at 7.5.

* * * * *